United States Patent [19]

Field et al.

[11] Patent Number: 5,256,799
[45] Date of Patent: Oct. 26, 1993

[54] PREPARATION OF 6-HYDROXYINDOLINES AND THEIR USE FOR PREPARATION OF NOVEL LASER DYES

[75] Inventors: George F. Field, Danville; Peter R. Hammond, Livermore, both of Calif.

[73] Assignee: The United States of Americas as represented by the United States Department of Energy, Washington, D.C.

[21] Appl. No.: 913,084

[22] Filed: Jul. 14, 1992

[51] Int. Cl.$^5$ .............................. C07D 215/20
[52] U.S. Cl. ..................... 548/469; 548/508
[58] Field of Search ................ 548/508, 469

[56] References Cited

U.S. PATENT DOCUMENTS 3,888,818  6/1975  Deblandre ............... 548/508 X
3,932,415  1/1976  Reynolds .
4,622,400  11/1986  Hammond .

FOREIGN PATENT DOCUMENTS 63-211264  9/1988  Japan .

OTHER PUBLICATIONS

Hideo Tanaka, et al., "A Facile Synthesis of 4-Hydroxy-and 4-Aminoindoles Through Corresponding Indolines", The Chemical Society of Japan, 1989; vol. 62, No. 11, pp. 3742–3744.
R. R. Hunt, et al., "A New Synthesis of Methoxyindoles", J. Chem. Soc. (C), 1966, pp. 344–345.
Jutta Arden, et al., "Fluorescence and Lasing Properties of Rhodamine Dyes", Journal of Luminescence 48 & 49 (1991) pp. 352–358.
1990 American Chemical Society Database Search listing 10 references, 15 pages.

Primary Examiner—Marianne M. Cintins
Assistant Examiner—Catherine Scalzo
Attorney, Agent, or Firm—Isabelle R. McAndrews; Roger S. Gaither; William R. Moser

[57] ABSTRACT

A novel method for the synthesis of 6-hydroxyindolines and new fluorescent dyes produced therefrom, which dyes are ring-constrained indoline-based rhodamine class dyes. These dyes have absorption and emission spectra which make them particularly useful in certain dye laser applications.

11 Claims, No Drawings

PREPARATION OF 6-HYDROXYINDOLINES AND THEIR USE FOR PREPARATION OF NOVEL LASER DYES

The United States Government has rights in this invention pursuant to Contract No. W-7405-ENG-48 between the United States Department of Energy and the University of California Lawrence Livermore National Laboratory.

BACKGROUND OF THE INVENTION

The present invention relates to a novel method for the synthesis of new fluorescent dyes, and more specifically to a method for producing novel dyes which are ring-constrained indoline-based rhodamine class dyes. These compounds have absorption and emission spectra which make them particularly useful in certain dye laser applications.

An important intermediate necessary for the efficient synthesis of these dyes is 6-hydroxyindoline.

Known methods for the synthesis of 6-hydroxyindolines are circuitous (R. R. Hunt, R. L. Rickard, "A new synthesis of methoxyindoles," *J. Chem. Soc.* (C) 1966, 344; M. Julia, H. Gaston-Breton, "recherches en série indolique. XVII.—Préparation de quelques indolines, indoles et typtamines oxygénesen positions -4 ou -6 par cyclisation <arynique>" *Bull Soc. Chem. France* 1966, 1335), and a known method for synthesizing the methyl derivative involves an expensive and dangerous hydride reaction (CIBA Ltd., "1-Alkyl-6-carbamoyloxyindolines" Brit. Patent 726,078 (Mar. 16, 1955). Yet another method, known as the Leimgruber-Batcho method, can be used for indole synthesis ((a) P. L. Feldman, H. Rapport, "Convenient synthesis of 6-methoxyindole and 6-methoxytryptophyl bromide," *Synthesis* 1988, 735; (b) A. D. Batcho, W. Leimgruber, *Org. Synth.* 1963, 63, 214) followed by a problematic and expensive reduction to the indoline (G. W. Gribble, J. H. Hoffman, *Synthesis* 1977, 859). Separately, 4-hydroxyindoline has been produced (H. Tanaka, Y. Murakami, T. Aizawa, S. Torii, "A facile synthesis of 4-hydroxy- and 4-aminoindoles through corresponding indolines," *Bull. Chem. Soc. Jpn.* 1989, 62, 3742).

Thus, it is an object of the invention to identify and efficiently synthesize new compounds which are indoline-based rhodamine class dyes having absorption and emission spectra appropriate for utility in dye lasers.

It is a further object of the invention to identify a simpler, safer and less expensive method of producing such dyes through the 6-hydroxyindoline intermediate.

SUMMARY OF THE INVENTION

In order to attain these objects, the present invention is directed to new method for preparing 6hydroxyindolines of the formula:

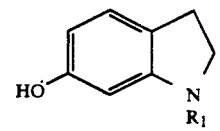

where $R_1$ is hydrogen or lower alkyl, preferably $C_1$ to $C_4$, and the use thereof to synthesize dyes of the general formula:

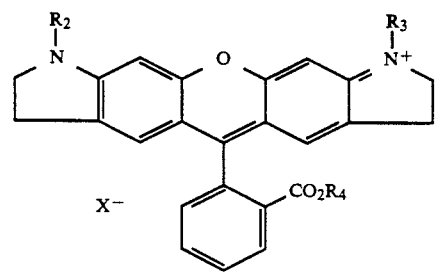

wherein $R_2$, $R_3$ and $R_4$ are hydrogen (but not all three at the same time, a known compound) or lower alkyl and wherein anion $X^-$ is halide, fluoroborate, trifluoromethanesulfonate or perchlorate.

In a preferred embodiment of the invention, $R_2$ and $R_3$ are hydrogen and $R_4$ is lower alkyl, preferably $C_1$ to $C_4$. In another preferred embodiment $R_2$, $R_3$ and $R_4$ are all lower alkyl, preferably $C_1$ to $C_4$. These compounds have characteristics properties making them especially suited for particular wavelengths of laser operation.

DETAILED DESCRIPTION OF THE INVENTION

The most preferred embodiments of the invention will now be described in detail.

SYNTHESIS GENERALLY DESCRIBED

The following charts illustrate the novel synthesis of 6-hydroxyindoline according to the invention:

Chart I

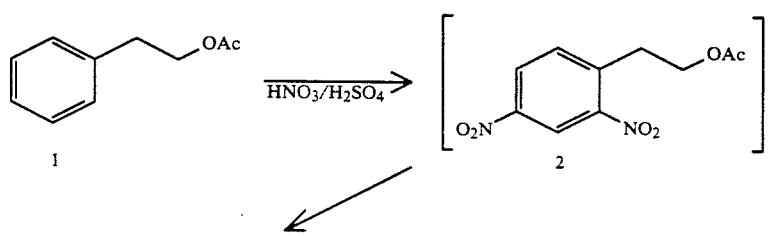

Chart I

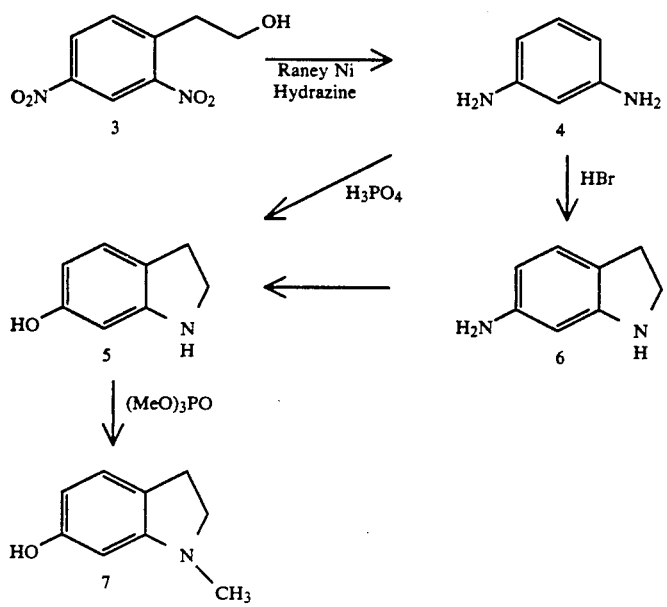

In the synthesis shown in Chart I phenethyl acetate 1 is an inexpensive starting material. The nitration of phenethyl acetate was found to proceed satisfactorily (70% after recrystallization) at higher concentrations than reported in the literature thus facilitating large scale production. Reduction of the nitro groups proceeded well with hydrazine hydrate and Raney nickel, obviating the need for pressure equipment. The reaction is extremely vigorous and is much more easily controlled in addition of hydrazine hydrate to a mixture of the dinitro compound and Raney nickel in ethanol rather than by addition of Raney nickel to the other two components as was done in the literature. V. G. Sinyavskii and R. A. Kornienoko, *J. Org. Chem.* (USSR) 1970 6, 1229.

Attempted ring closure of 4 with phosphoric acid under the high temperature conditions (220°) specified in the Japanese paper for 4-hydroxyindoline led to complex tarry mixtures from which 6-hydroxyindoline could not be isolated; however, we find that at 160° 6-hydroxyindoline 5 is formed in good yield. Temperatures of from about 150° to about 180° can be used.

The N-methyl derivative was prepared by methylation with trimethyl phosphate. W. A. Sheppard in "Organic Synthesis Collective vol. 5", H. E. Baumgarten, ed., New York; John Wiley & Sons 1973, p. 1805. See also P. R. Hammond, E. J. Schimitachek, J. A. Trias, U.S. Pat. No. 4,138,901, and Hammond and Atkins, J. Heterocyclic Chem 12 1061 (1975).

Following the synthesis of 6-hydroxyindoline, synthesis of the dyes shown in chart II follows the route of condensation of phthalic anhydride with a maminophenol, followed by esterification of the intermediate acid:

Chart II

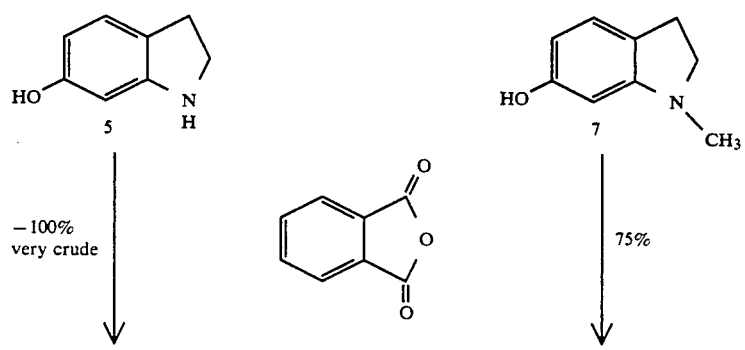

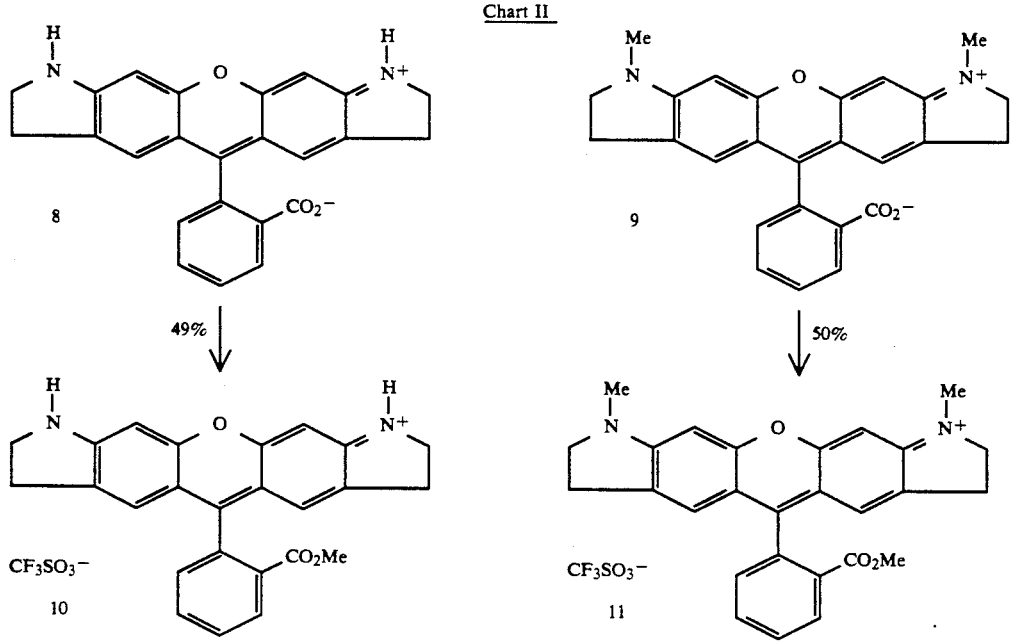

Synthesis of the intermediate carboxylic acid 8 was accomplished in a manner similar to that described by G. A. Reynolds, "Prylium dyes having a fused rigidized nitrogen-containing ring," U.S. Pat. No. 3,932,415, using zinc chloride as condensing agent. Although the total weight obtained was close to theoretical, it was contaminated with a large amount of an unidentified by-product which could be separated only after esterification. Esterification was straightforward and the dye product could be isolated as triflate, 10, by crystallization from methanol.

The phosphoric acid method of condensation gave the acid intermediate 9, in satisfactory yield. Likewise esterification with methanol/trifluoromethanesulfonic acid proceeded normally to give 11.

COMPLETE EXPERIMENTAL DETAILS

A. Preparing 6-Hydroxyindolines

The following procedures were used to prepare the compounds used in the process of the present invention.

Synthesis of 2-(2,4-Dinitrophenyl)-ethanol 3. A mixture of 400 ml (9 mole) of 90% nitric acid and 500 ml of concentrated sulfuric acid (9.2 mole) contained in a 2 l 3-necked flask fitted with magnetic stirrer, thermometer, addition funnel and condenser was cooled in a dry ice/isopropyl alcohol bath to $-12°$. (If the temperature is lower, the stirring becomes inefficient and puffs of nitrous fumes are emitted with each drop.) Dropwise addition of 200 ml (1.2 mol) of phenethyl acetate 1 required 2 hr 40 min. The internal temperature was held between $-5°$ and $-15°$ by controlling the rate of addition of ester and addition of dry ice to the bath. The bath was then replaced with an ice/water bath and the reaction mixture was allowed to stand for 70 min. The reaction mixture was poured onto 2 kg of ice and extracted with 2 l of toluene in two portions. The toluene extracts were combined and washed with 600 ml of saturated sodium carbonate solution. The organic phase was separated, dried over sodium sulfate and concentrated in vacuo to leave 318.8 g of yellow oil. This oil was dissolved in 1 l of methanol. To the solution was added 200 ml of concentrated hydrochloric acid. The solution was heated under reflux for 4 hr and then concentrated in vacuo to about 500 g. To the residue was added 200 ml of saturated sodium carbonate solution. Needles precipitated. The solution was still strongly acidic. The solid was collected, (the solid discolors on contact with metal spatulas) slurried with 500 ml of water, collected and rinsed with water to give 247 g (97%) of yellowish solid, mp 55°–65°. From the mother liquor (on standing) was obtained an additional 7 g of product. The two crops were combined and recrystallized twice from about 500 ml of warm toluene, (the warmed toluene solution dissolves plastic funnels) to give 175 g (69%) of product 3, mp 71°–75° (lit. 69°–70°, E. Uhlmann and W. Pfleiderer, *Helv. Chim. Acta* 1981, 64, 1698). Purity was also established by thin layer chromatography on silica gel plates using ethyl acetate o 50% ethyl acetate/hexane as eluents.

Synthesis of 2-(2,4-Diaminophenyl)ethanol 4. To 10.3 g of Raney nickel slurry which had been washed with methanol by decantation and 400 ml of methanol contained in a 2 l 3-necked flask fitted with thermometer, dropping funnel, efficient condenser and magnetic stirrer was added 84.86 g (0.4 mol) of 2-(2,4-dinitrophenyl)-ethanol 3. The mixture was put under an atmosphere of nitrogen. A solution of 80 ml (1.65 mol) of hydrazine hydrate in 80 ml of methanol was added drop wise during 1 hr. There is a pronounced exotherm (if the Raney nickel has not been washed with methanol, there is an induction period when the hydrazine is added and the initial exotherm is difficult to control) and the mixture foams vigorously. After 45 min the exothermicity had subsided and a heating mantle was added to maintain reflux in the reaction mixture. The reaction mixture was held at reflux for 1 hr after the addition of hydrazine was complete. At this time the evolution of gas was very slow. The reaction mixture was cooled and filtered through Celite to remove the catalyst. The filtrate was concentrated in vacuo and the residue was reconcentrated twice with toluene to leave 64 g of black oil. This was crystallized from 50 ml of ethyl acetate. The solid was collected after standing overnight in the refrigerator to give 59.34 g (97%) of crude product 4 as a grey solid, mp 67°-72°. Recrystallization from 550 ml of ethyl acetate with two large spatula-fulls of charcoal gave 49.64 g (81%) of tan solid, mp 75°-79° (lit. 76°-77°, V. G. Sinyavskii and R. A. Kornienko, *J. Org. Chem.* (*USSR*) 1970 6, 1229).

It also forms a crystalline oxalate from methanol, mp 143°-150° with decomposition.

Synthesis of 6-Hydroxyindoline 5. A mixture of 800 g of 70% (w/w) phosphoric acid (made by diluting 659 g of 85% phosphoric acid to 800 g with water) and 80 g of 2-(2,4-diaminophenyl)ethanol 4 was placed in a 1 liter Parr bomb and heated at 160°±5° for 20 hr. For this step acids other than phosphoric could be used, i.e. the step requires an aqueous strong acid such as phosphoric, sulfuric, methanesulfonic, trifluoromethanesulfonic, hydrobromic and the like.

Approximately 40 lb of pressure was developed. The cooled reaction mixture was diluted to 1 1 with ice and water. It was partially neutralized by the addition of about 350 ml of 40%(w/w) of sodium hydroxide. A dark tar separated which was filtered off through Celite. Addition of about 300 ml more sodium hydroxide solution precipitated a brown solid. The pH was about 6. The solid was collected and rinsed with water. It weighed 56.51 g (80%), mp 113°-116° (lit. 112°-113°, R. R. Hunt and R. L. Rickard, *J. Chem. Soc.* (*C*), 1966, 344), after drying overnight. The combined aqueous filtrates were extracted with 1000 ml of ethyl acetate in two portions. The organic extracts were dried over sodium sulfate and concentrated in vacuo to give 6.1 g of an oil which solidified.

A sample recrystallized from toluene with charcoal had mp 115°-120°.

An alternative method of forming 5 from compound 4 would be to use stronger acid to avoid the use of the constant volume conditions, i.e. using 85% phosphoric acid at atmospheric pressure.

An alternative route to the hydroxyindoline 6 is to prepare 6-aminoindoline from compound 4 using HBr and then using a strong aqueous acid, such as phosphoric acid, to convert the amino group to the hydroxy counterpart, as follows.

Preparation of 6-aminoindoline 6. A mixture of 24 g (0.16 mol) of crude 2-(2,4-diaminophenyl)ethanol 4 and 200 ml of 48% hydrobromic acid is heated under reflux for 4 hr and then concentrated in vacuo to leave 109.5 g of a brown semicrystalline mass which is cooled overnight in the refrigerator. The solid is collected and rinsed with ethanol to give 38.66 g (83% if dihydrobromide) of light tan solid.

A mixture of 2 g of the hydrobromide and 10 ml of saturated sodium carbonate solution was made strongly alkaline with 1 ml of con. ammonium hydroxide and extracted with 30 ml of ethyl acetate in 3 portions. The organic phases were combined washed with 13 ml of brine and dried over sodium sulfate. Concentration in vacuo left 0.77 g (85%) of brown oil. This oil and 0.56 g of similar material was purified by filtration through 20 ml of silica gel in methylene chloride. The silica was washed with 50 ml of methylene chloride and two 50 ml portions of ethyl acetate. Solid material (1.1 g) was obtained from hexane. That from the first fraction had mp 72°-76° and its nmr was consistent with the expected structure.

6-Hydroxyindoline 5 from 6-Aminoindoline 6 - A mixture of 5 g of 6-aminoindoline and 100 g of 30% (w/w) phosphoric acid was stirred and heated in an autoclave at 170°-175° for 15 hr. The light brown solution was cooled to room temperature and neutralized with 40 ml of 40% sodium hydroxide solution. It was further diluted to 300 ml with water. The precipitated phosphate salts were filtered off and washed with 200 ml of ethyl acetate in two portions. The organic extracts were separated, combined, washed with 100 ml of brine, dried over sodium sulfate and concentrated in vacuo to leave 4.08 g of red brown oil. This oil was crystallized from hexane to give 3.11 g of crude 6-hydroxyindoline, mp 110°-110°, as an orange colored solid.

Preparation of N-Methyl-6-hydroxyindoline 7. To 37.78 g (0.286 mol) of 6-hydroxyindoline 5 in a 100 ml round-bottom flask fitted with a magnetic stirrer, thermometer and condenser connected to a source of nitrogen was added 13.38 ml (16.02 g, 0.114 mol) of trimethyl phosphate. It was then placed in an oil bath and heating was commenced. The bath temperature reached 105° in 10 min. Then the reaction mixture became homogeneous and shortly thereafter an exotherm occurred. The flask was removed periodically from the oil bath to keep the internal temperature below 150°. The reaction was heated at 140°-150° for 2 hr. Thin layer chromatography on silica gel plates eluted with 50% Ethyl acetate/hexane or 4% methanol/methylene chloride showed that starting material was still present and 3 ml (3.59 g, 25.6 mmol) more of trimethyl phosphate was added. Heating was continued at 155° for 1.5 hr. The reaction mixture was allowed to cool and then dissolved in 100 ml of saturated sodium carbonate solution and 100 ml of methylene chloride with warming in portions. The aqueous phase was separated and washed with 2×100 ml of methylene chloride. The organic phases were combined, washed with 200 ml of half-saturated brine, dried over sodium sulfate and concentrated in vacuo to leave 28.6 g (67%) of dark tar. This was dissolved in methylene chloride and filtered through 300 ml of silica gel in methylene chloride. A total of 800 ml of methylene chloride eluate and then 400 ml of ethyl acetate was collected. Concentration and collection of the residue from hexane gave 18.29 g (43%) of crude product 7 as a brown solid which was used for the preparation of 9.

B. Preparation of Rhodamine Dyes

Synthesis of the dyes 10 and 11 of Chart II follows the standard route of condensation of phthalic anhydride with m-aminophenol followed by the esterification of the intermediate acid.

Preparation of 11-(2-Carboxyphenyl) dipyrrolino[3,2-b;2,3-i]xanthylilum chloride 8.

a) This synthesis was accomplished using the method of U.S. Pat. No. 3,932,415, as follows: A mixture of 2.7 g (20 mmol) of 6-hydroxyindoline 5, 7.41 g (50 mmol) of phthalic anhydride and 1.6 g (11.7 mmol) of zinc chloride was mixed and heated in an oil bath at 165°±5° for 5 hr with occasional stirring. The melt was cooled, powdered and triturated with 100 ml of warm water. The solid was dissolved in 150 ml of warm 1 N sodium hydroxide. The solution was filtered through Celite and acidified with 15 ml of concentrated hydrochloric acid. The fine brick-red precipitate was collected and washed with water to give 5.43 g of crude product. The theoretical yield of zwitterion 8 is 3.82 g.

b) A mixture of 13.52 g (0.1 mol) of 6-hydroxyindoline 5, 37.02 g (0.25 mol) of phthalic anhydride and 8.2 g (0.06 mol) of zinc chloride was mixed and heated in an oil bath at 165°±5° for 4 hr with stirring. The melt was cooled. The sublimed phthalic anhydride was scraped out and discarded. The solid residue (56.36 g) was powdered and stirred for 2 hr with 500 ml of water. The solid was collected, rinsed with water and dissolved in 750 ml of warm 1 N sodium hydroxide. After 1 hr the solution was filtered and acidified with stirring with 50 ml of concentrated hydrochloric acid. Only a small amount of fine dark material precipitated. The solution was clarified by vacuum filtration through Celite. The filtrate was acidified with 10 ml of glacial acetic acid. A finely divided brick-red precipitate formed. The mixture was stirred overnight. The solid was collected and rinsed with water. It filtered only very slowly. The solid was stirred with 300 ml of warm (60°) methanol for 1 hr and collected to give 21.81 g (theory: 19.12 g for the zwitterion) of red solid. UV: 522 nm (apparent $\epsilon = 34,000$).

Preparation of the methyl ester 10.

a) To a stirred mixture of 5.8 g of the crude acid above, 65 ml of methanol was added dropwise 5 ml of trifluoromethanesulfonic acid. This mixture was stirred and heated under reflux for 12 hr when TLC (silica gel developed with HOAc/MeOH/CH$_2$Cl$_2$ 1:5:45 or 10% triethylamine in ethanol) showed little starting material left. The reaction mixture was cooled, diluted with 75 ml of saturated sodium bicarbonate solution and cooled overnight in the refrigerator. The solid was collected to give 4.3 g of still damp black material. This solid was chromatographed on 100 ml of silica gel packed in 5% methanol/methylene chloride. Elution with 200 ml of 10% methanol/methylene chloride gave 2.7 g (theory from 6-hydroxy indoline 5: 5.46 g or 49% for the two steps) of impure product.

Two pure fractions were combined and recrystallized from methanol to give 0.16 g of 10 as purple crystals, mp 320° decomposition. For analysis a sample was dried at 60° for 18 hr.

Anal. Calcd. for $C_{26}H_{21}F_3N_2O_6S$: C, 57.14; H, 3.87; N, 5.13. Found: C, 56.84; H, 3.90; N, 5.11.

b) To a stirred mixture of 37.6 g (97.1 mmol) of crude 8, in 400 ml of methanol was added dropwise 40 ml of trifluoromethanesulfonic acid. This mixture was stirred and heated under reflux for 19 hr. It was allowed to come to room temperature and then cooled in the refrigerator for 3 hr. The precipitated purple solid was collected and rinsed with methanol to give 13.18 g (25% of product 10).

This product was recrystallized by dissolution of 15.9 g in 1.2 l of boiling methanol, filtration, concentration to 800 ml and cooling overnight in the refrigerator. The solid was collected and rinsed with methanol to give 13.01 g of 10 as purple needles. Purity established using thin layer chromatography on silica gel developed with HOAc/MeOH/CH$_2$Cl$_2$ 1:5:45 or 10% triethylamine in ethanol.

Preparation of 11-(2-Carboxyphenyl)di-N-methylpyrrolino[3,2-b;2,3-i]xanthylilum chloride 9. A mixture of 9 g (60 mmol) of 6-hydroxy-N-methylindoline 7 and 13.5 g (91 mmol) of phthalic anhydride was stirred and heated in an oil bath under nitrogen at 145°–150° for 4.5 hr. The mixture melted and set up after about 10 min. It later got fluid again. To it was added 9.2 g (60 mmol) of 6-hydroxy-N-methylindoline 7 and 15 ml of 85% phosphoric acid. It was stirred and heated at 150° for 3 hr. After it had cooled slightly 50 ml of methanol was added through the condenser and it was heated briefly under reflux. It was then cooled in the refrigerator overnight. The finely divided solid was collected and rinsed with methanol to give 19.12 g (75%) of crude product 9.

Preparation of the methyl ester 11. To a stirred mixture of 29.86 g (71.9 mmol) of 9, and 300 ml of methanol was added dropwise 30 ml (339 mmol) of trifluoromethanesulfonic acid. The reaction mixture was stirred and heated under reflux for 23 hr at which time thin layer chromatography using HOAc/MeOH/CH$_2$Cl$_2$ in a ratio of 1:5:45 or 10% triethylamine in ethanol showed little or no 9. It was cooled overnight in the refrigerator. The solid was collected, rinsed with methanol and dried overnight in the refrigerator. The solid was collected, rinsed with methanol and dried overnight to give 25.03 g (61%) of 11, mp 256°–260°. This material combined with 15g from a similar experiment was recrystallized from 300 ml of methanol to give 33.93 g of 11.

An analytical sample was prepared by recrystallization from methanol was obtained as green gold plates, mp 261°–264° (sinter ca. 240°).

Anal. Calcd. for $C_{28}H_{25}F_3N_2O_6S \cdot H_2O$ (mw 592.60): C, 56.72; H, 4.59; N, 4.73; H$_2$O, 3.04.

Found: C, 56.34; H, 4.58; N, 4.72; H$_2$O, 2.95 (Karl Fischer).

For photophysical measurements a sample was recrystallized again from methanol this time with the use of charcoal.

The foregoing description of the preferred embodiments of the invention are intended to be illustrative and not exhaustive. Many variations of the disclosed inventions are possible in light of the present disclosure, and it is intended that such variations within the skill of those familiar with this art are included within the scope of the following claims.

What is claimed is:

1. A method of preparing 6-hydroxyindolines of the formula:

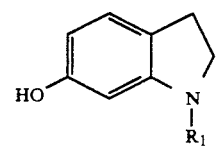

where R$_1$ is hydrogen or lower alkyl, comprising the steps of:
    (a) treating phenethyl acetate with a nitrating agent to form an intermediate of 2-(2,4-dinitrophenyl)-acetate;
    (b) converting said intermediate to 2-(2,4-dinitrophenyl)-ethanol;
    (c) reducing said 2-(2,4-dinitrophenyl)-ethanol to form 2-(2,4-diaminophenyl)-ethanol; and
    (d) reacting said 2-(2,4-diaminophenyl)-ethanol with a strong aqueous acid and at a temperature of from about 140° C. to 180° C. to form 6-hydroxyindoline.

2. A method as in claim 1 wherein said strong aqueous acid is selected from the group consisting of phosphoric, sulfuric, methanesulfonic, trifluoromethanesulfonic and hydrobromic acids.

3. A method as in claim 1 wherein said strong aqueous acid is 70% w/w phosphoric acid, and step (d) occurs under constant volume conditions.

4. A method as in claim 1 wherein said strong aqueous acid is 85% w/w phosphoric acid, and step (d) occurs at atmospheric pressure.

5. A method as in claim 1, further comprising the step of:
(e) reacting said 6-hydroxyindoline, wherein $R_1$ is H, with a $C_1$-$C_4$ alkylating agent to form N-[$C_1$-$C_4$]-6-hydroxyindoline.

6. A method as in claim 5 wherein said alkylating agent is a methylating agent.

7. A method as in claim 6, wherein said methylating agent is trimethyl phosphate.

8. A method as in claim 1, wherein the reaction of step (d) occurs at less than 170° C.

9. A method as in claim 1, wherein the reduction of step (c) is with hydrazine catalyzed by Raney metal.

10. A method of preparing 6-hydroxyindolines of the formula:

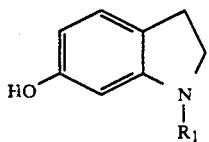

where $R_1$ is hydrogen or lower alkyl, comprising the steps of:
(a) treating phenethyl acetate with a nitrating agent to form an intermediate of 2-(2,4-dinitrophenyl)-acetate;
(b) converting said intermediate to 2-(2,4-dinitrophenyl)-ethanol;
(c) reducing said 2-(2,4-dinitrophenyl)-ethanol to form 2-(2,4-diaminophenyl)-ethanol;
(d) reacting said 2-(2,4-diaminophenyl)-ethanol with hydrobromic acid to form 6-aminoindoline; and
(e) reacting said 6-aminoindoline with phosphoric acid at a temperature of about 170° C. to form 6-hydroxyindoline.

11. A method of preparing 6-hydroxyindolines of the formula:

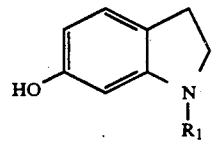

where $R_1$ is a lower alkyl, comprising the steps of:
(a) treating phenethyl acetate with a nitrating agent to form an intermediate of 2-(2,4-dinitrophenyl)-acetate;
(b) converting said intermediate to 2-(2,4-dinitrophenyl)-ethanol;
(c) reducing said 2-(2,4-dinitrophenyl)-ethanol to form 2-(2,4 diaminophenyl)-ethanol; and
(d) reacting said 2(2,4-diaminophenyl)-ethanol with a strong aqueous acid and at a temperature of from about 140° C. to 180° C. to form 6-hydroxyindoline.

* * * * *